United States Patent [19]

Hayakawa

[11] Patent Number: 5,641,908
[45] Date of Patent: Jun. 24, 1997

[54] ULTRASONIC DIAGNOSTIC APPARATUS

[75] Inventor: Kenichi Hayakawa, Kawasaki, Japan

[73] Assignee: Fujitsu Limited, Kawasaki, Japan

[21] Appl. No.: 552,574

[22] Filed: Nov. 3, 1995

[30] Foreign Application Priority Data

Apr. 12, 1995 [JP] Japan ................... 7-086799

[51] Int. Cl.$^6$ ................................. H01P 3/00
[52] U.S. Cl. ............... 73/620; 310/316; 310/317; 128/661.01; 128/660.07; 128/662.06
[58] Field of Search ............ 73/625, 626, 861.25, 73/620, 627, 660.04, 660.05, 660.07, 661.07, 661.08, 661.09, 661.01, 662.02, 662.03, 662.06; 310/316, 317; 367/903; 364/413.25

[56] References Cited

U.S. PATENT DOCUMENTS

| | | |
|---|---|---|
| 4,954,960 | 9/1990 | Lo et al. ................... 364/484 |
| 5,087,850 | 2/1992 | Suzuta ......................... 310/316 |
| 5,146,192 | 9/1992 | Kondo et al. ................ 73/626 |
| 5,198,713 | 3/1993 | Suzuta ......................... 310/316 |

*Primary Examiner*—Hezron E. Williams
*Assistant Examiner*—Rose M. Miller
*Attorney, Agent, or Firm*—Staas & Halsey

[57] ABSTRACT

There is provided an ultrasonic diagnostic apparatus in which ultrasonic waves are transmitted into a subject. The ultrasonic waves are reflected within the subject. The reflected waves are received and an image based on the reflected waves is displayed. In the ultrasonic diagnostic apparatus, a resonance frequency and/or a Q value of a resonance circuit are altered in accordance with conditions and/or an operation of a handler. Thus, it is possible to adapt to various uses with few probes.

11 Claims, 13 Drawing Sheets

ULTRASONIC DIAGNOSTIC APPARATUS

BACKGROUND OF THE INVENTION

1. Field of the Invention

The present invention relates to an ultrasonic diagnostic apparatus in which ultrasonic waves are transmitted into the subject to obtain received signals through receiving ultrasonic waves reflected within a subject, thereby displaying an image based on the received signals.

2. Description of the Related Art

Hitherto, there has been used an ultrasonic diagnostic apparatus in which ultrasonic waves are transmitted toward the subject, specially a living body, ultrasonic waves reflecting from a tissue within a living body are received to generate received signals, and tomographic image of the living body is displayed on the basis of the received signals, thereby facilitating a diagnostic of diseases of the viscus inner organ or the like in the living body. According to such an ultrasonic diagnostic apparatus, usually, there is also provided such a function that a blood flow distribution within the living body as the subject is evaluated on the basis of received signals obtained through a plurality of number of times of receiving and transmitting of the ultrasonic waves in the same direction within the subject. The blood flow distribution thus obtained is displayed on the basis of the received signals.

FIG. 15 is a typical illustration showing the state of operations of an ultrasonic diagnostic apparatus. FIG. 16 is a block diagram showing a schematic circuit construction of an ultrasonic diagnostic apparatus according to the related art. In the following figures, the same parts are denoted by the same reference numbers as those of FIGS. 15 and 16.

In FIG. 15, an operator 100 puts a tip portion 20a of a probe 20 on the subject 200. On the tip portion 20a, there is mounted a piezo-electric transducer 21 (FIG. 16). On the rear end of the probe 20 there is provided a connector 22 detachably connected with a main body 10 of the ultrasonic diagnostic apparatus. The connector 22 and the tip portion 20a of the probe 20 are connected to each other through a cable 23. As the cable 23, in order to avoid intermixing of noises, generally, there is adopted a coaxial cable.

When the operator 100 operates a handler on a panel 12 of the main body 10, a transmission circuit 13 of the main body 10 generates high voltage pulses, which are applied through a signal line 23a within the cable 23 of the probe 20 to the piezo-electric transducer 21. Upon receipt of the high voltage pulses, the piezo-electric transducer 21 transmits ultrasonic waves into the subject 200. The ultrasonic waves transmitted from the piezo-electric transducer 21 are reflected within the subject and returned to the piezo-electric transducer 21. The ultrasonic waves thus received by the piezo-electric transducer 21 are converted into electrical received signals. The received signals are fed through the signal line 23a of the cable 23 to a receive circuit 14 within the main body 10 so as to be suitably amplified. The thus amplified received signals are subjected to a suitable signal processing in a signal processing circuit 15 and then fed to a display unit 16 in which a tomographic image within the body of the subject 200 is displayed on a display screen 11 (FIG. 15).

In the signal processing circuit 15, there is evaluated a velocity of a blood flow on each portion within the tomographic plane on the basis of the received signal obtained through a plurality of number of times of transmitting and receiving in the same direction within the body of the subject 200. In the display unit 16, for example, a velocity distribution of the blood flow is color-displayed upon superposing it on the above-mentioned tomographic image.

Incidentally, a fundamental technology for obtaining tomographic images and a velocity distribution of the blood flow is well known. Also, with respect to the point that what circuit algorithm is used for evaluating the tomographic images and the velocity distribution of the blood flow, it is not essential matter for the present invention. Thus, additional explanation as to how the tomographic images and the velocity distribution of the blood flow are evaluated will be omitted.

It is noted that such states that the apparatus is adjusted in its entirety to obtain the tomographic images and the velocity distribution of the blood flow are referred to as "B-mode" and "Doppler mode", respectively.

As shown in FIG. 16, the signal line 23a of the cable 23 has a capacitance component 24, and the piezo-electric transducer 21 itself also has a capacitance component. Hence, there is such a problem that the received signals obtained in the piezo-electric transducer 21 will be remarkably attenuated owing to their capacitance components while transferred to the receive circuit 14. Specifically, the received signals obtained in the piezo-electric transducer 21 are high frequency of signals associated with the frequency of ultrasonic waves and thus are remarkable in attenuation. In addition, since such received signals are ones obtained through receipt of the ultrasonic waves reflected within the body of the subject 200 (FIG. 15), the received signals involved in the ultrasonic waves especially reflected on the depth portions within the body are extremely weak. Thus, the attenuation of the received signals has a large effect on the resolution of the images obtained and the like.

FIGS. 17, 18 and 19 are each a view useful for understanding a measure to be taken for preventing an attenuation of the received signals. In those figures, the same parts are denoted by the same reference numbers.

According to an example shown in FIG. 17, an inductive component (inductor) 31 is connected in parallel with the capacitance component 24 so as to constitute a resonance circuit 30. The resonance circuit 30 serves to prevent an attenuation of received signals having a frequency corresponding to that of the ultrasonic waves.

According to an example shown in FIG. 18, the inductor 31 is incorporated into the tip portion 20a of the probe 20 to constitute a resonance circuit 30 in the combination use with the capacitance component of the piezo-electric transducer. In addition, the receive circuit 14 is also incorporated into the tip portion 20a of the probe 20. In this case, an attenuation of the received signals due to the capacitance component of the piezo-electric transducer 21 can be prevented by the incorporation of the inductor 31. Further, since the capacitance component 24 of the cable 23 is located in the lower stage side of the receive circuit 14, there is no problem.

According to an example shown in FIG. 19, in comparison with that of FIG. 17, a resistance element 32 is connected in series with the inductor 31. The measures according to the examples shown in FIGS. 17 and 18 involve a high Q value of the resonance. Thus, there is such a fear that a ringing of the received signals continues for a long time and then time resolution (resolution in a depth direction within the subject) will be deteriorated. In view of this, generally, there is adopted a technique in which the resistance element 32 for dumping is connected as shown in FIG. 19 to suppress the Q value.

According to the related art as described above, it is possible to contribute to the improvement in sensitivity on a specific frequency on a fixing basis (prevention of an attenuation of the received signals). On the other hand, it should be noticed, however, that the improvement in a sensitivity and the time resolution are in a relation of the trade-off. In addition, in view of the fact that for example, in the B-mode, the improvement of the time resolution may bring a better image while making somewhat the sacrifice of the sensitivity. However, in the Doppler mode, it is desirable that the sensitivity is improved even making somewhat the sacrifice of the time resolution. Therefor, there is a case such that it is not preferable to adjust fixedly on a one way basis the resonance circuit. To satisfy these matters using the conventional technique, there is a need to prepare a number of probes which are adjusted for every use. This causes the cost to be increased and also the maintenance and the management to be troublesome.

SUMMARY OF THE INVENTION

In view of the foregoing, it is therefore an object of the present invention to provide an ultrasonic diagnostic apparatus capable of adapting to various uses with few probes.

To achieve the above-mentioned objects, according to the present invention, there is provided a first ultrasonic diagnostic apparatus comprising a probe having a signal transmission cable and a piezo-electric transducer for transmitting and receiving ultrasonic waves, said piezo-electric transducer being mounted on a tip of said signal transmission cable, and a main body for displaying images within a subject on the basis of received signals generated in such a manner that ultrasonic waves are transmitted from said piezo-electric transducer into the subject and the ultrasonic waves reflected within the subject are received by said piezo-electric transducer, a rear end of said probe being connected to said main body, said ultrasonic diagnostic apparatus further comprising:

a resonance circuit arranged in such a manner that at least a part of capacitance components of a transmission path for the received signals forms a constituting element of the resonance circuit, said resonance circuit being located within said probe or extending through said probe and said main body, and permitting at least one of a resonance frequency and a Q value to be altered; and a resonance characteristic altering unit for altering at least one of the resonance frequency and the Q value of the resonance circuit in accordance with conditions.

In the ultrasonic diagnostic apparatus as mentioned above, said resonance characteristic altering unit may alter at least one of the resonance frequency and the Q value of the resonance circuit in accordance with at least one selected from among a diagnostic mode, a frequency of ultrasonic waves, a kind of said probe, time elapsed for receiving of ultrasonic waves and a focal length, as said conditions.

Here, while the "diagnostic mode" is not restricted to a specific mode classification, it refers to, for example, the above-mentioned B-mode and Doppler mode.

To achieve the above-mentioned objects, according to the present invention, there is provided a second ultrasonic diagnostic apparatus comprising a probe having a signal transmission cable and a piezo-electric transducer for transmitting and receiving ultrasonic waves, said piezo-electric transducer being mounted on a tip of said signal transmission cable, and a main body for displaying images within a subject on the basis of received signals generated in such a manner that ultrasonic waves are transmitted from said piezo-electric transducer into the subject and the ultrasonic waves reflected within the subject are received by said piezo-electric transducer, a rear end of said probe being connected to said main body, said ultrasonic diagnostic apparatus further comprising:

a resonance circuit arranged in such a manner that at least a part of capacitance components of a transmission path for the received signals forms a constituting element of the resonance circuit, said resonance circuit being located within said probe or extending through said probe and said main body, and permitting at least one of a resonance frequency and a Q value to be altered;

a handler; and a resonance characteristic altering unit for altering at least one of the resonance frequency and the Q value of the resonance circuit in accordance with an operation of said handler.

Here, while the second ultrasonic diagnostic apparatus does not matter where the handler is disposed, it is preferable that the handler is disposed on a tip portion of the probe, the piezo-electric transducer being mounted on said tip portion of the probe.

In the first ultrasonic diagnostic apparatus and the second ultrasonic diagnostic apparatus of the present invention, it is one aspect that said resonance circuit is provided with a variable capacitance diode, and said resonance characteristic altering unit alters the resonance frequency of the resonance circuit through controlling a voltage to be applied to said variable capacitance diode.

In the first ultrasonic diagnostic apparatus and the second ultrasonic diagnostic apparatus of the present invention, it is another aspect that said resonance circuit is provided with an inductor and a variable resistance, which are mutually connected in series and disposed between the signal transmission cable of said probe and a ground, and said resonance characteristic altering unit alters the Q value of the resonance circuit through controlling a resistance value of said variable resistance.

To achieve the above-mentioned objects, according to the present invention, there is provided a third ultrasonic diagnostic apparatus comprising a probe having a signal transmission cable and a piezo-electric transducer for transmitting and receiving ultrasonic waves, said piezo-electric transducer being mounted on a tip of said signal transmission cable, and a main body for displaying images within a subject on the basis of received signals generated in such a manner that ultrasonic waves are transmitted from said piezo-electric transducer into the subject and the ultrasonic waves reflected within the subject are received by said piezo-electric transducer, a rear end of said probe being connected to said main body, said ultrasonic diagnostic apparatus further comprising:

a resonance circuit arranged in such a manner that at least a part of capacitance components of a transmission path for the received signals forms a constituting element of the resonance circuit, said resonance circuit being located within said probe or extending through said probe and said main body, and permitting at least one of a resonance frequency and a Q value to be altered;

a handler; and a resonance characteristic altering unit for altering at least one of the resonance frequency and the Q value of the resonance circuit in accordance with conditions and an operation of said handler as well.

The first ultrasonic diagnostic apparatus of the present invention is provided with the resonance characteristic altering unit for altering at least one of the resonance frequency and the Q value of the resonance circuit in accordance with conditions. This feature makes it possible to adapt to, for example, any of the B-mode and the Doppler mode with a single probe.

The second ultrasonic diagnostic apparatus of the present invention is provided with the handler and the resonance characteristic altering means for altering at least one of the resonance frequency and the Q value of the resonance circuit in accordance with an operation of said handler. This feature makes it possible, in a similar fashion to that of the first ultrasonic diagnostic apparatus, to adapt to, for example, any of the B-mode and the Doppler mode with a single probe. In this case, as to the handler, there is no need to provide a handler involving a complicated handling, and it is sufficient to provide, for example, a switch or the like adapted to switch between the B-mode use and the Doppler mode through turning on and off thereof. Mounting the handler on the tip portion of the probe permits an operator to manually operate with the same hand as that grasping the tip portion, thereby improving operational efficiency.

The third ultrasonic diagnostic apparatus of the present invention is provided with the handler and the resonance characteristic altering means for altering at least one of the resonance frequency and the Q value of the resonance circuit in accordance with conditions and an operation of said handler. This feature makes it possible to perform a fine adjustment of characteristics of the resonance circuit altered in accordance with the condition. In view of the fact that properties (e.g. an intensity and the center frequency) of the received signals are varied in accordance with the depth on which ultrasonic waves are reflected within the subject, in a case where the characteristic of the resonance circuit is altered in accordance with, for instance, as the condition, time elapsed for receiving of ultrasonic waves, which corresponds to the depth on which ultrasonic waves are reflected within the subject, there is a need to correct the characteristic of the resonance circuit, for instance, when the ultrasonic diagnostic is performed as to the abdomen of a pregnant woman, since amniotic fluid involves less attenuation of the ultrasonic waves. In such a case, the use of the above-mentioned handler makes it possible to easily perform the correction of the characteristic of the resonance circuit.

DESCRIPTION OF THE PREFERRED EMBODIMENTS

Hereinafter, there will be described embodiments of the present invention.

Figure 1:
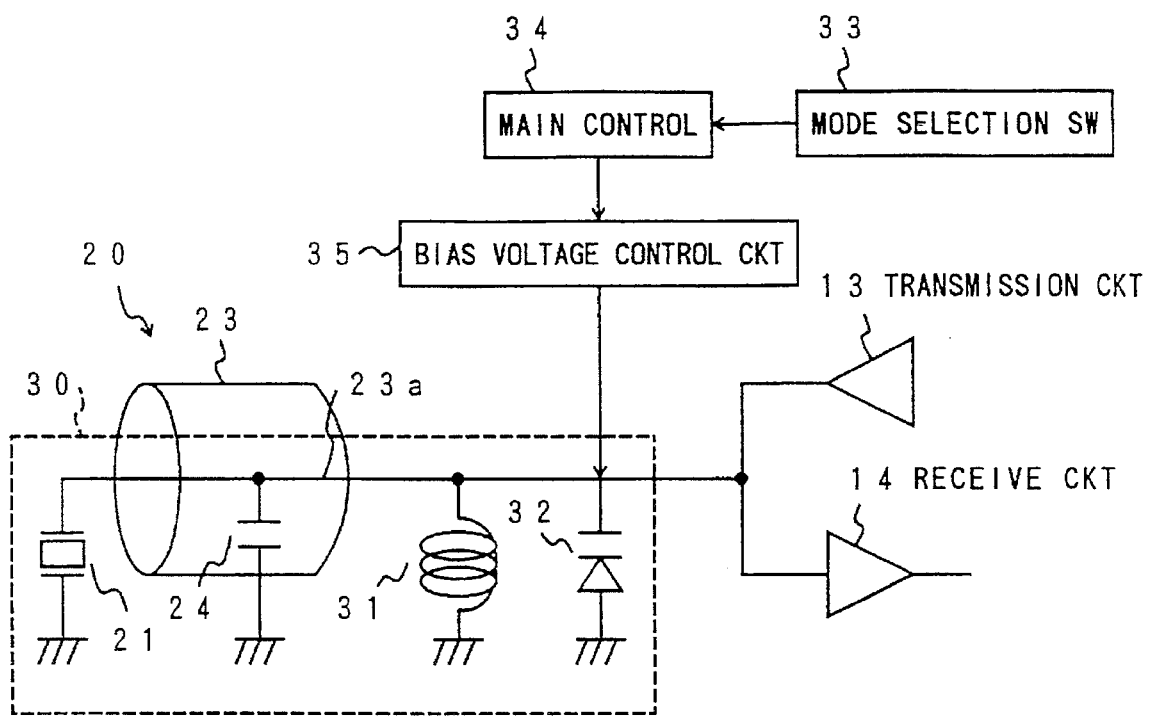
FIG. 1 is a circuit diagram of main parts of the first embodiment of the present invention.

FIG. 1 is a circuit diagram of main parts of the first embodiment of the present invention. In the following figures, the same parts are denoted by the same reference numbers as those of FIGS. 15 to 19.

According to the first embodiment shown in FIG. 1, the inductor 31 and a variable capacitance diode 32 are added for the capacitance component of the piezo-electric transducer 21 and the capacitance component 24 of the signal line 23a of the cable 23 to constitute the resonance circuit 30. It is acceptable that the inductor 31 and the variable capacitance diode 32 are disposed either inside the probe 20, or inside the main body 10.

Figure 15:
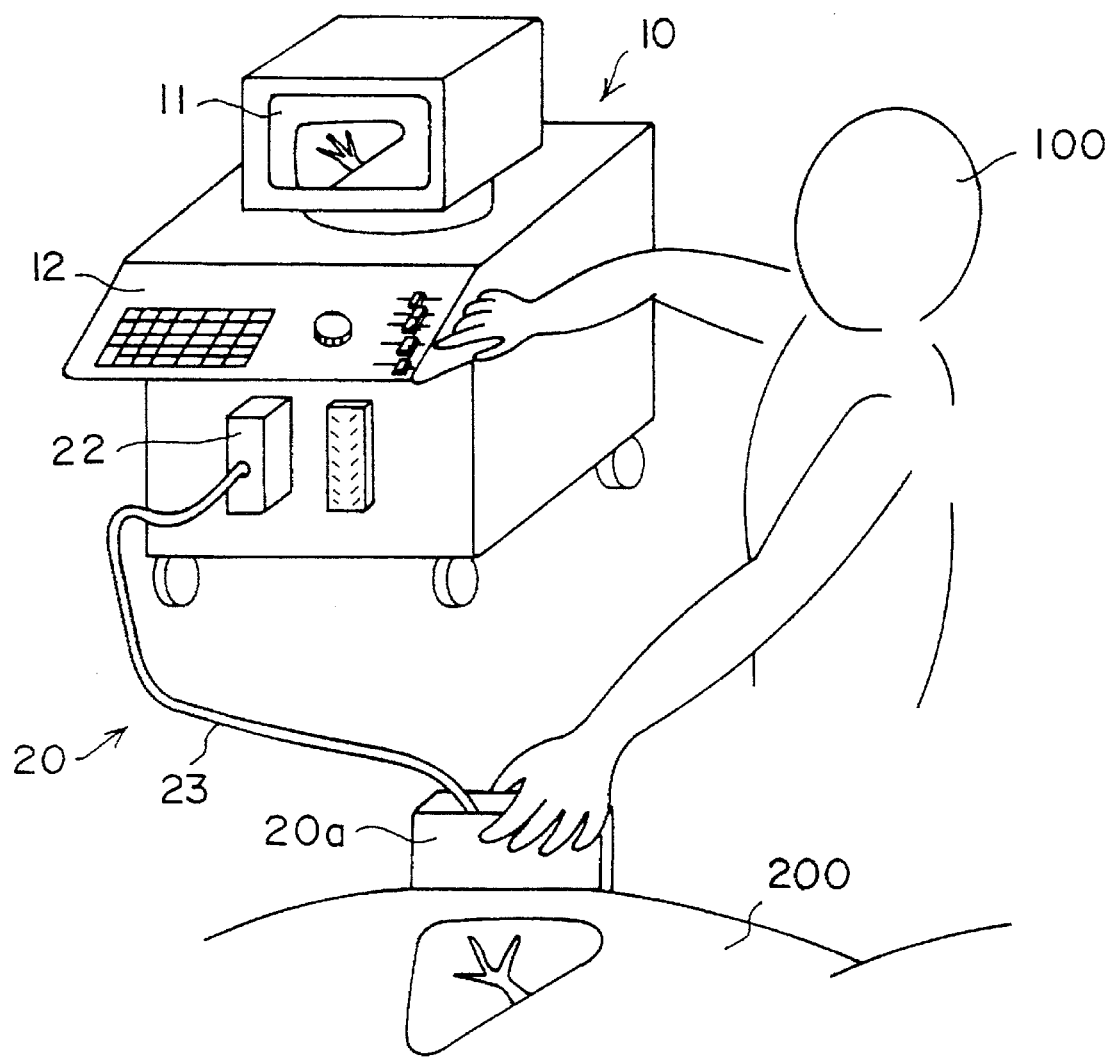
FIG. 15 is a typical illustration showing the state of operations of an ultrasonic diagnostic apparatus.
Figure 16:
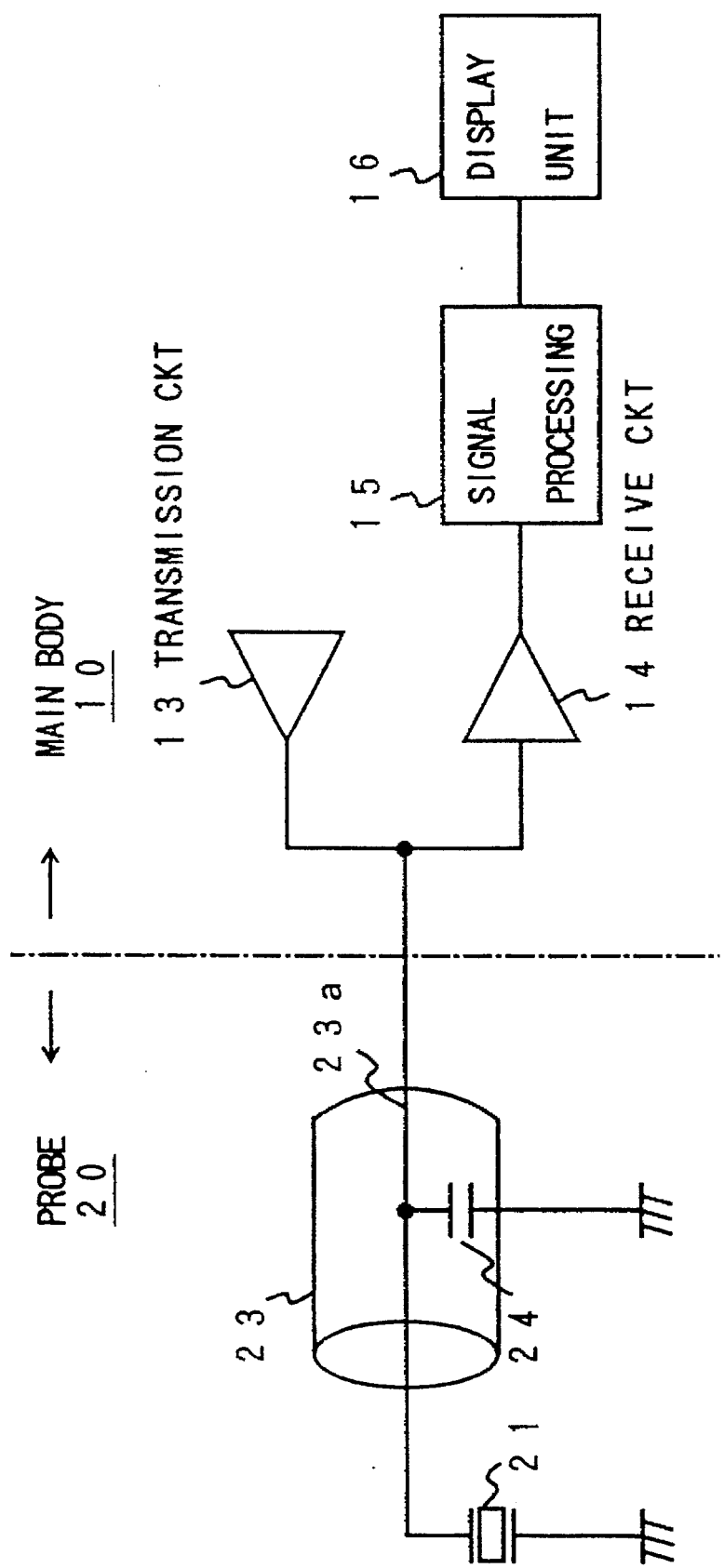
FIG. 16 is a block diagram showing a schematic circuit construction of an ultrasonic diagnostic apparatus.
Figure 17:
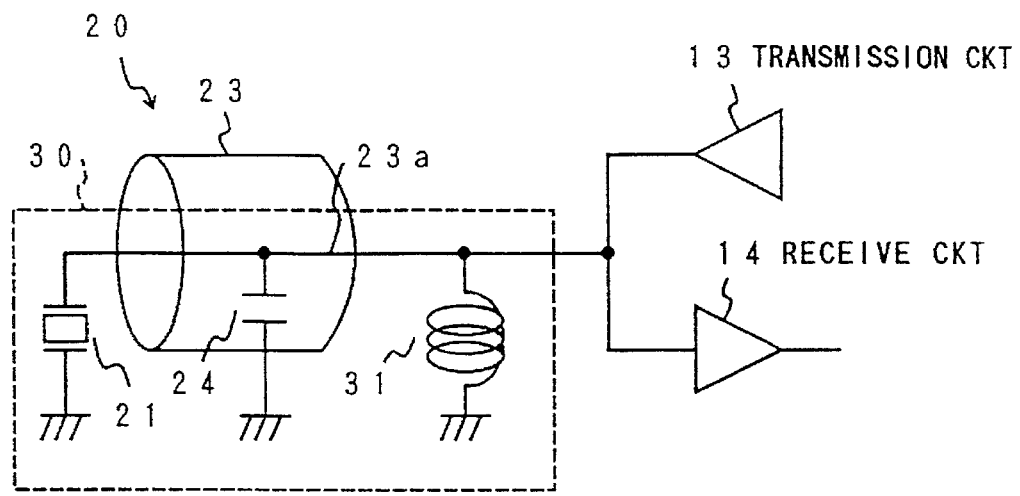
FIG. 17 is a view useful for understanding a measure to be taken for preventing an attenuation of the received signals.
Figure 18:
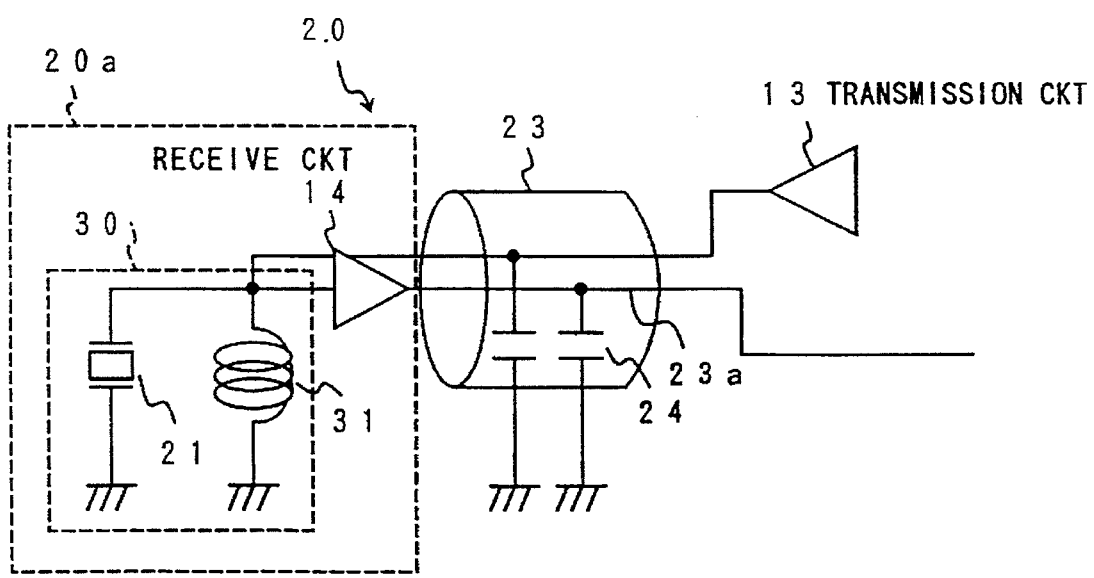
FIG. 18 is a view useful for understanding another measure to be taken for preventing an attenuation of the received signals.
Figure 19:
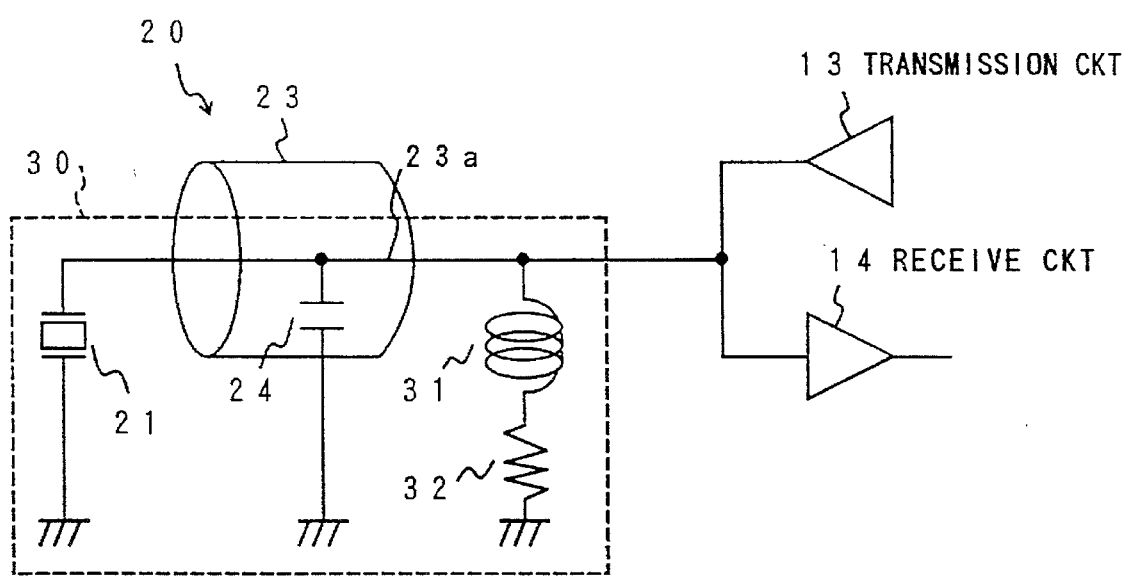
FIG. 19 is a view useful for understanding still another measure to be taken for preventing an attenuation of the received signals.

Further, according to the first embodiment, a mode selection switch 33 is provided on, for example, an operation panel (cf. operation panel 12 in FIG. 15).

The mode selection switch 33 serves to switch between the B-mode and the Doppler mode. Operation information of the mode selection switch 33 is fed to a main control unit 34 which carries the overall control of the ultrasonic diagnostic apparatus. The main control unit 34 controls the ultrasonic diagnostic apparatus in its entirety to adapt for the mode selected between the B-mode and the Doppler mode. As one of the ways of the control, the main control unit 34 issues a command to a bias voltage control circuit 35 to control a DC bias of the signal line 23a. Upon receipt of the command, the bias voltage control circuit 35 applies the adjusted bias to the signal line 23a. Thus, a capacitance of the variable capacitance diode 32 is varied in accordance with a level of the DC bias, so that a resonance frequency $f_r$ of the resonance circuit 30 is varied.

Figure 2:
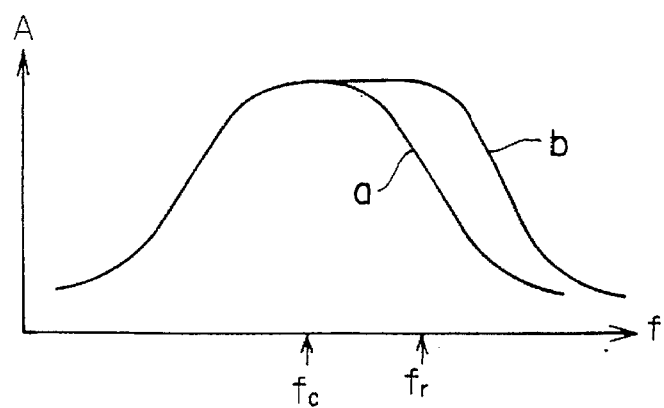
FIG. 2 is a view useful for understanding how to adjust a resonance frequency in the B-mode, in the first embodiment shown in FIG. 1.
Figure 3:
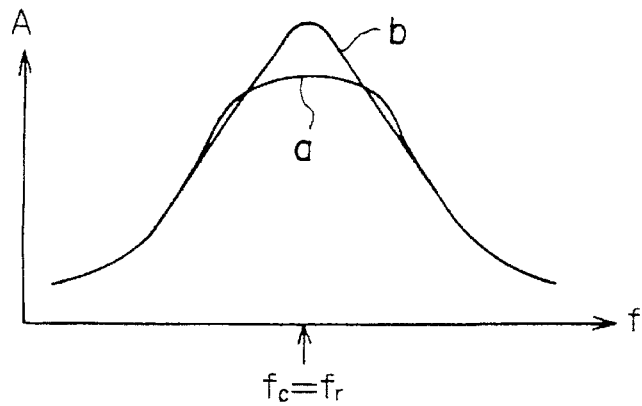
FIG. 3 is a view useful for understanding how to adjust a resonance frequency in the Doppler mode, in the first embodiment shown in FIG. 1.

FIGS. 2 and 3 are views useful for understanding how to adjust resonance frequencies in the B-mode and the Doppler mode in the first embodiment shown in FIG. 1, respectively.

In those figures, the axes of abscissas indicates a frequency f, and the axes of ordinates indicates a gain (sensitivity). A frequency $f_c$ is representative of the center frequency of the ultrasonic waves; a frequency $f_r$ a resonance frequency of the resonance circuit; a graph a a characteristic of the received signals in case of no resonance circuit (in a case where the inductor 31 and the variable capacitance diode 32 in FIG. 1 are removed); and a graph b a characteristic of the received signals in a case where the resonance circuit is controlled to be set up to the resonance frequency $f_r$.

In case of the B-mode, it is preferable to obtain an image excellent in resolution as to a time direction (depth direction) through spreading a ratio band of the received signals so that wide frequency band of received signals can be obtained. Thus, in case of the B-mode, as shown in FIG. 2, a DC bias is controlled by the bias voltage control circuit 35 so that the resonance frequency $f_r$ of the resonance circuit is set up to a frequency shifted from the center frequency $f_c$.

On the other hand, in case of the Doppler mode, it is possible to evaluate a blood flow distribution with greater precision through obtaining high sensitive received signals. Thus, in case of the Doppler mode, as shown in FIG. 3, a DC bias is controlled by the bias voltage control circuit 35 so that the resonance frequency $f_r$ of the resonance circuit coincides with the center frequency $f_c$ of the ultrasonic waves.

Figure 4:
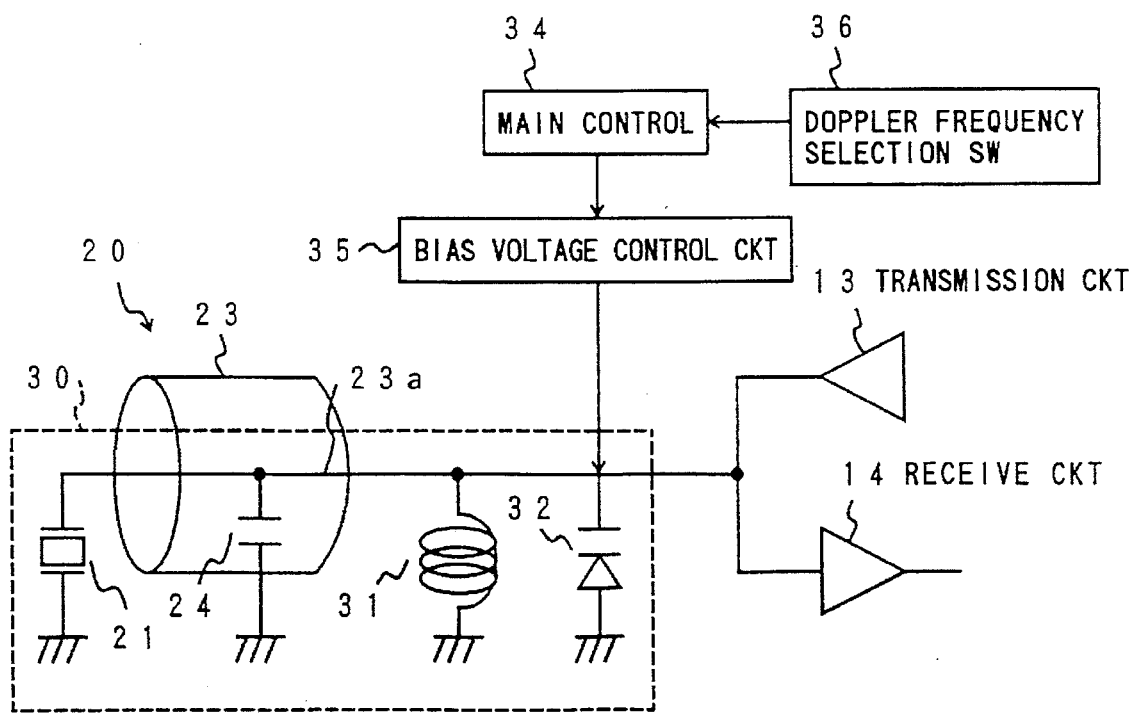
FIG. 4 is a circuit diagram of main parts of the second embodiment of the present invention.
Figure 5:
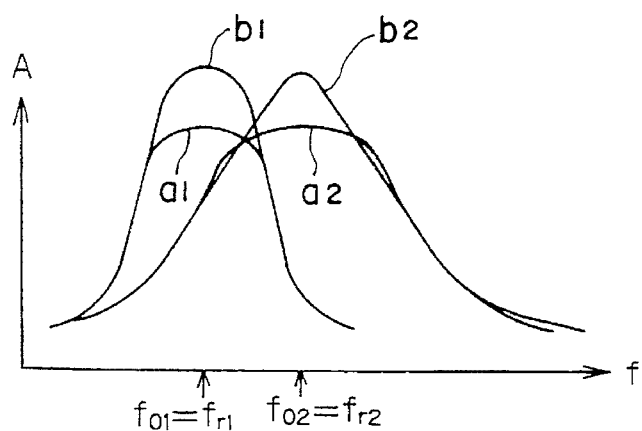
FIG. 5 is a view useful for understanding how to adjust a resonance frequency in the resonance circuit, in the second embodiment shown in FIG. 4.

FIG. 4 is a circuit diagram of main parts of the second embodiment of the present invention. FIG. 5 is a view useful for understanding how to adjust a resonance frequency in the resonance circuit, in the second embodiment shown in FIG. 4.

According to the second embodiment shown in FIG. 4, there is provided a Doppler frequency selection switch 36 instead of the mode selection switch 33 in the first embodiment shown in FIG. 1.

In the Doppler mode, since the ultrasonic waves are easy to attenuate in a case where a diagnostic depth is deep, it happens that a lower frequency of ultrasonic waves is used in comparison with a case that a diagnostic depth is shallow. According to the present embodiment, the Doppler frequency selection switch 36 is switched in accordance with a diagnostic depth of interest, so that a pulse width of the high voltage pulse transmitted from the transmission circuit 13 is varied. Thus, the center frequency $f_c$ of the ultrasonic waves transmitted from the piezo-electric transducer 21 is converted, when the depth of interest is deep, into a low frequency $f_{o1}$ and when the depth of interest is shallow, into a high frequency $f_{o2}$. According to the present embodiment, further, the bias to be applied to the variable capacitance diode 32 is varied by the bias voltage control circuit 35, so that the resonance frequency $f_r$ of the resonance circuit 30 is altered in accordance with the depth of interest to frequencies $f_{r1}$ or $f_{r2}$ which are the same as the center frequency $f_{o1}$ and $f_{o2}$ of the ultrasonic waves, respectively. Thus, according to the present embodiment, as shown in FIG. 5, it is possible to obtain high sensitivity characteristics (graphs b1 and b2) in comparison with the case of no resonance circuit (graphs a1 and a2).

Figure 6:
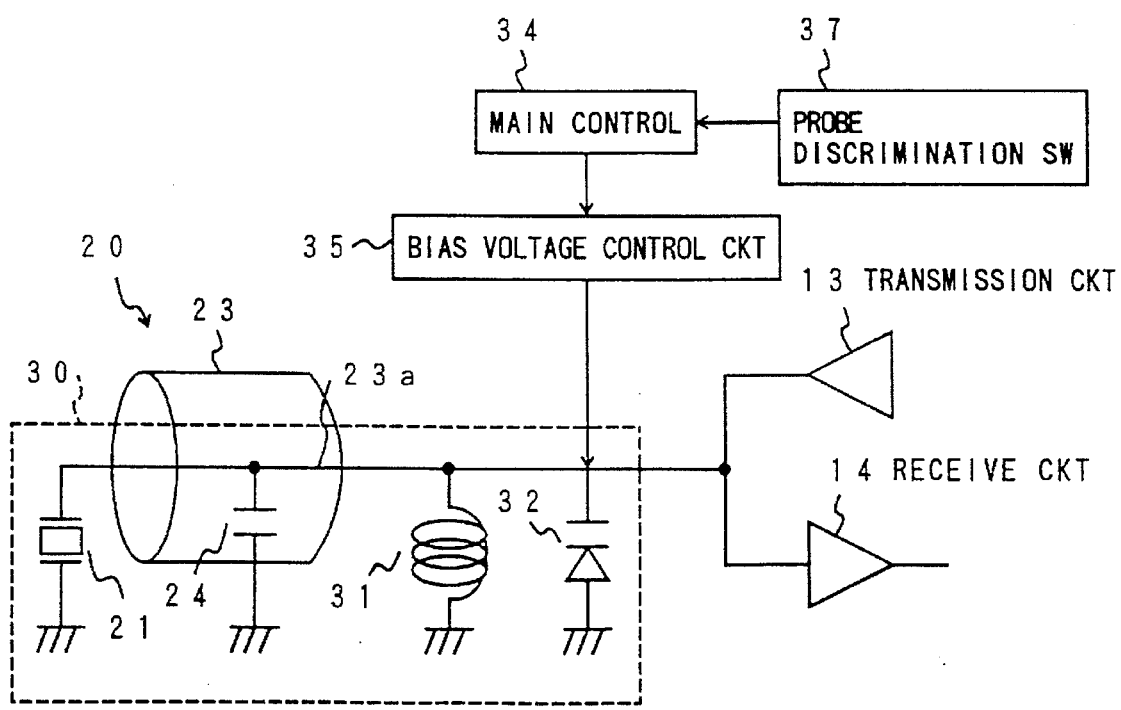
FIG. 6 is a circuit diagram of main parts of the third embodiment of the present invention.

FIG. 6 is a circuit diagram of main parts of the third embodiment of the present invention.

According to the third embodiment shown in FIG. 6, there is provided a probe discrimination switch 37 instead of the mode selection switch 33 in the first embodiment shown in FIG. 1.

In case of the diagnostic of a circulatory organ such as the heart, it is considered that the sensitivity and the direction resolution are important rather than the ratio band. On the other hand, in case of the diagnostic of a abdomen organ, it is considered that the ratio band is important rather than the sensitivity and the direction resolution. In this manner, the performance considered to be important is varied depending upon the diagnostic site. Further, in general, the probe 20 is varied depending upon the diagnostic site. Hence, as shown in FIG. 6, if there is provided such a control that the resonance frequency is varied in accordance with the probe 20 to be used, it will be possible to implement the improvement of the performance in compliance with the diagnostic site. While it is acceptable that there is so arranged that the probe discrimination switch 37 is disposed on the operation panel so that an operator may perform a switching operation, it is preferable that there is so arranged that the probe discrimination switch 37 is disposed on the connector 22 (FIG. 15) of the probe 20 or on a portion of the main body 10 to which portion the connector 22 is inserted, so that a kind of the probe 20 is automatically discriminated when the connector 22 is inserted.

Figure 7:
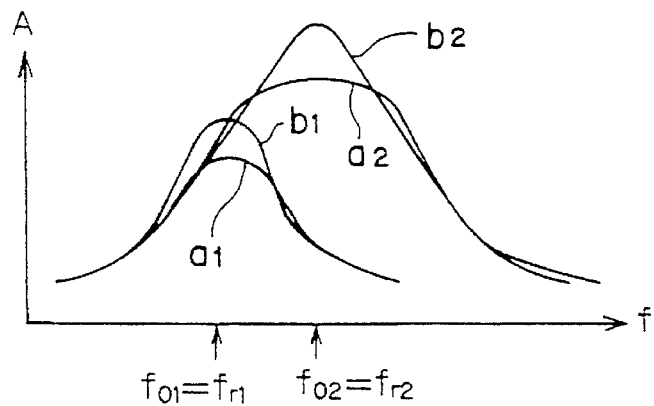
FIG. 7 is a view useful for understanding how to adjust a resonance frequency of the resonance circuit, in the fourth embodiment.

FIG. 7 is a view useful for understanding how to adjust a resonance frequency of the resonance circuit, in the fourth embodiment.

The ultrasonic waves transmitted from the piezo-electric transducer 21 is attenuated greater amount during travelling within the subject with higher frequency component. Hence, the center frequency $f_0$ of the ultrasonic waves returned to the piezo-electric transducer 21 is a lower frequency with the ultrasonic wave which is reflected at the deeper position within the subject and returns. In view of the fact that time required for returning of the ultrasonic wave to the piezo-electric transducer 21 corresponds to the reflection depth of the ultrasonic wave, the resonance frequency $f_r$ of the resonance circuit is varied in accordance with the center frequency $f_0$ of the ultrasonic waves (received signals) which is varied in accordance with the lapse of time, as shown in FIG. 7, thereby obtaining high sensitivity of signals throughout the wide areas from the shallow portion to the deep portion.

Figure 8:
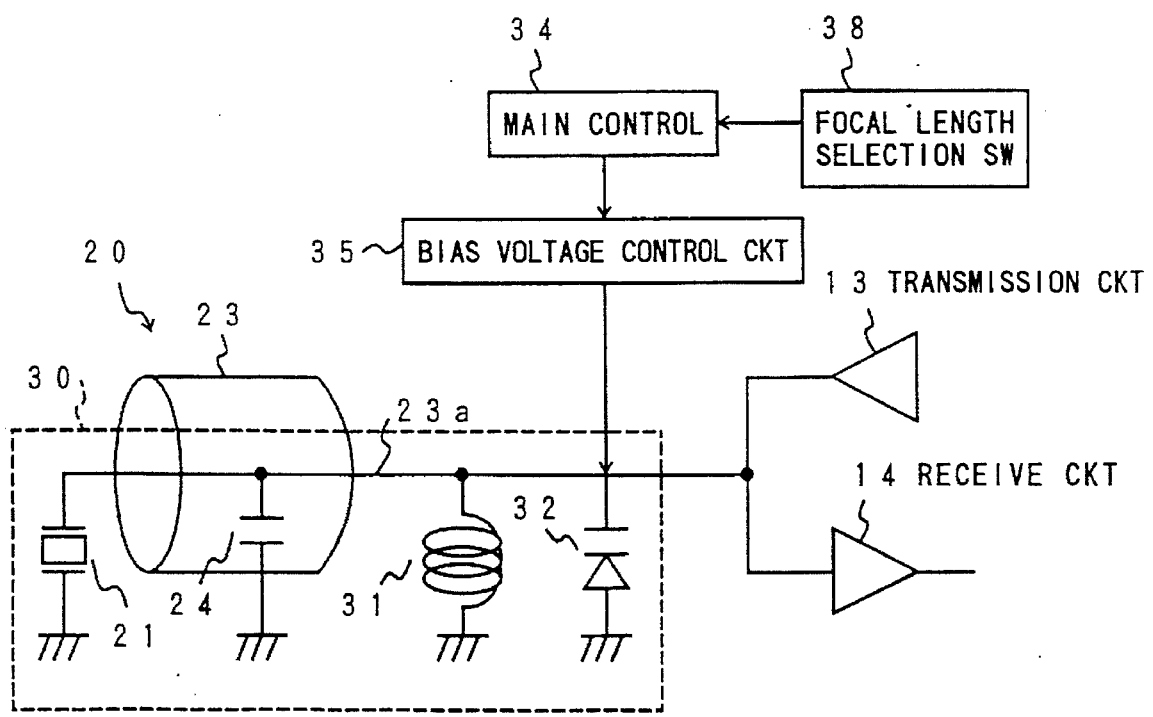
FIG. 8 is a circuit diagram of main parts of the fifth embodiment of the present invention.

FIG. 8 is a circuit diagram of main parts of the fifth embodiment of the present invention.

In an ultrasonic diagnostic apparatus using an array type of probe in which a plurality of piezo-electric transducers 21 are arranged, timing of high voltage pulses transmitted from the transmission circuit 13 to the respective piezo-electric transducers 21 is controlled, and in addition the received signals obtained by the respective piezo-electric transducers 21 are beamformed, thereby forming ultrasonic beams in which a focal point is formed at the optional depth within the subject. Incidentally, while the ultrasonic wave involves higher resolution with higher frequency, it involves a greater amount of attenuation.

Thus, as shown in FIG. 8, there is provided a focal length selection switch 38 for setting as to where a focal point is formed in depth within the subject, and there is provided such a control that when a focal point is set up at the deep portion within the subject, the resonance frequency is set up to be a high frequency, and when a focal point is set up at the shallow portion within the subject, the resonance frequency is set up to be a low frequency, thereby obtaining high sensitivity of received signals according to the focal length.

Figure 9:
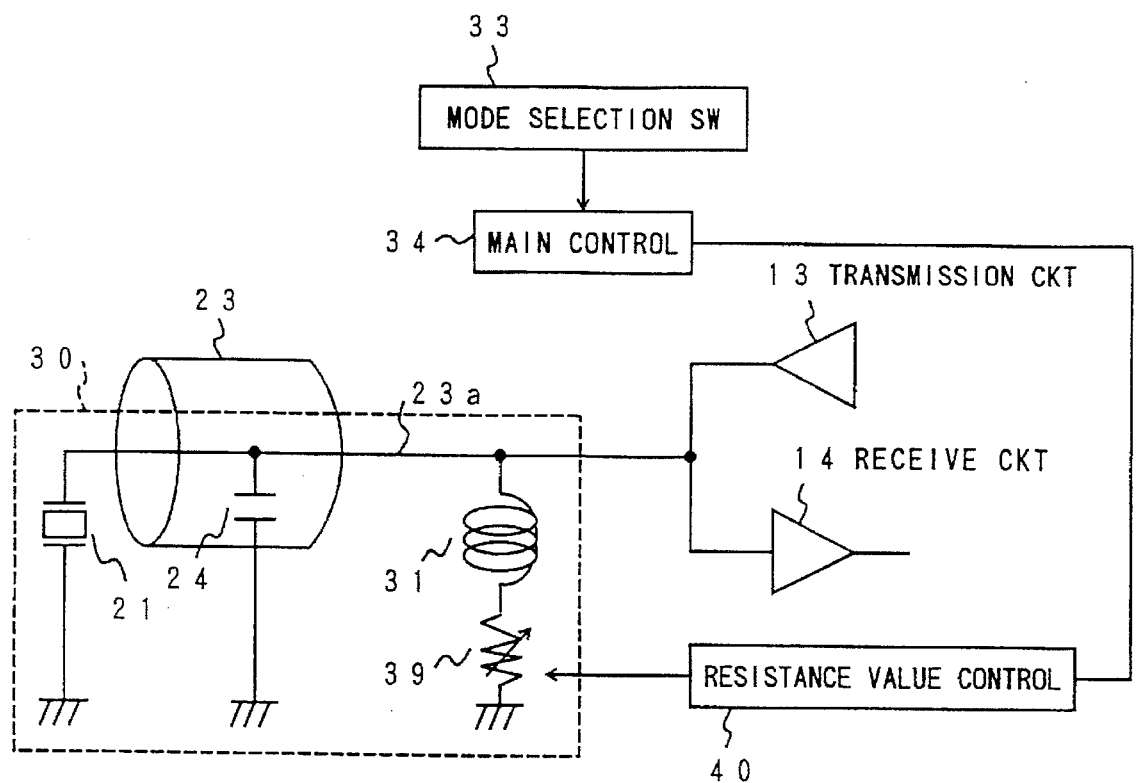
FIG. 9 is a circuit diagram of main parts of the sixth embodiment of the present invention.
Figure 10:
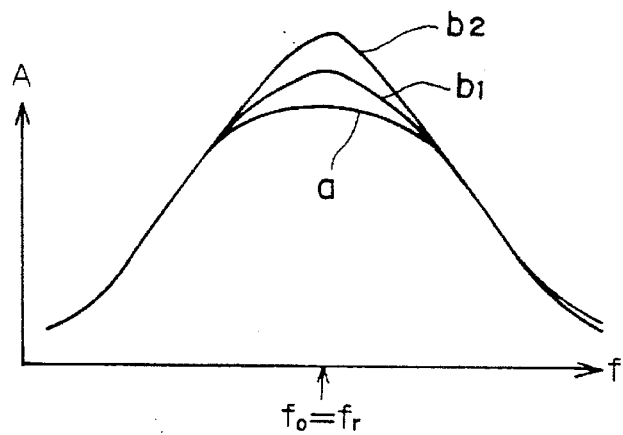
FIG. 10 is a view useful for understanding how to adjust the resonance circuit, in the sixth embodiment shown in FIG. 9.

FIG. 9 is a circuit diagram of main parts of the sixth embodiment of the present invention. FIG. 10 is a view useful for understanding how to adjust the resonance circuit, in the sixth embodiment shown in FIG. 9.

Now comparing the sixth embodiment shown in FIG. 9 with the first embodiment shown in FIG. 1, the variable capacitance diode 32 and the bias voltage control circuit 35 are omitted. Instead a variable resistance 39 is connected in series with the inductor 31, and in addition there is provided a resistance value control unit 40 for controlling a resistance value of the variable resistance 39.

As mentioned above, in the B-mode, it is preferable that a duration of the ringing of the received signals is shortened to improve a time resolution. In the Doppler mode, it is preferable that a sensitivity is emphasized while the time resolution is decreased somewhat. Thus, when the B-mode is selected by the mode selection switch 33, the resistance value of the variable resistance 39 is set up to be larger somewhat by the resistance value control unit 40, thereby shortening a duration of the ringing of the received signals upon saving the sensitivity as shown in graph b1 of FIG. 10. On the other hand, when the Doppler mode is selected by the mode selection switch 33, the resistance value of the variable resistance 39 is set up to be smaller somewhat by the resistance value control unit 40, thereby emphasizing the sensitivity as shown in graph b2 of FIG. 10. In this manner, it is possible to obtain an optimum characteristic according to the modes.

Figure 11:
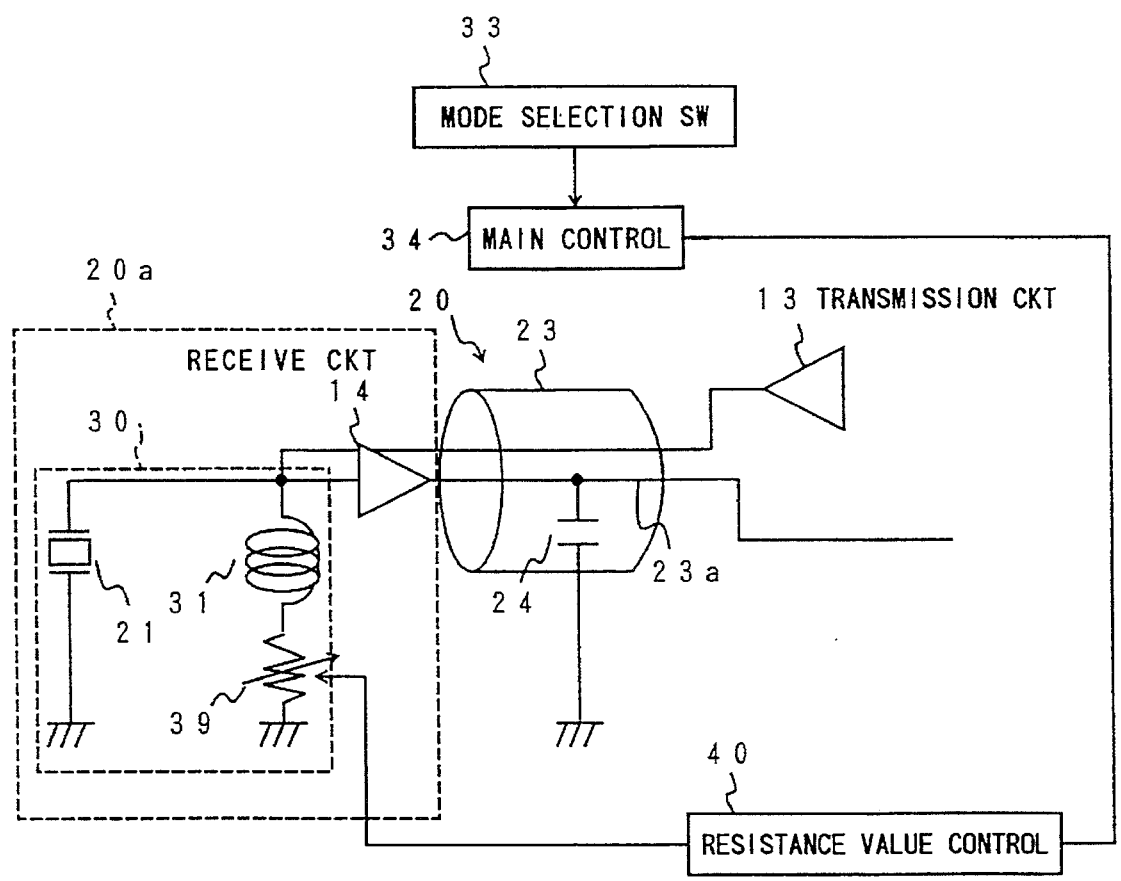
FIG. 11 is a circuit diagram of main parts of the seventh embodiment of the present invention.

FIG. 11 is a circuit diagram of main parts of the seventh embodiment of the present invention.

According to the seventh embodiment shown in FIG. 11, there is disposed the inductor 31, which constitutes the resonance circuit 30 in the combination use of the capacitance component of the piezo-electric transducer 21, within the tip portion 20a (FIG. 15) of the probe 20, and the variable resistance 39 is connected in series with the inductor 31. According to the seventh embodiment, the receive circuit 14 is also incorporated into the tip portion 20a of the probe 20. In this case, the attenuation of the received signals due to the capacitance component of the piezo-electric transducer 21 is prevented by the inductor 31 to emphasize the sensitivity. On the other hand, the capacitance component 24 of the cable 23 is located at the down-stream stage end of the receive circuit 14, and thus this involves no problem. With respect to the effects of the adjustment of the resistance value of the variable resistance 39 by the resistance value control unit 40, this is the similar to that of the sixth embodiment explained referring to FIGS. 9 and 10.

According to the sixth and seventh embodiments explained referring to FIGS. 9, 10 and 11, the mode selection switch 33 is provided, and the Q value of the resonance circuit is varied in accordance with switching of a diagnostic mode by the mode selection switch 33. However, the present invention is not restricted to those embodiments. It is acceptable that in a similar fashion to that of the second to fifth embodiments explained referring to FIGS. 4–8, the Q value of the resonance circuit 30 is varied in accordance with conditions other than the diagnostic mode.

Figure 12:
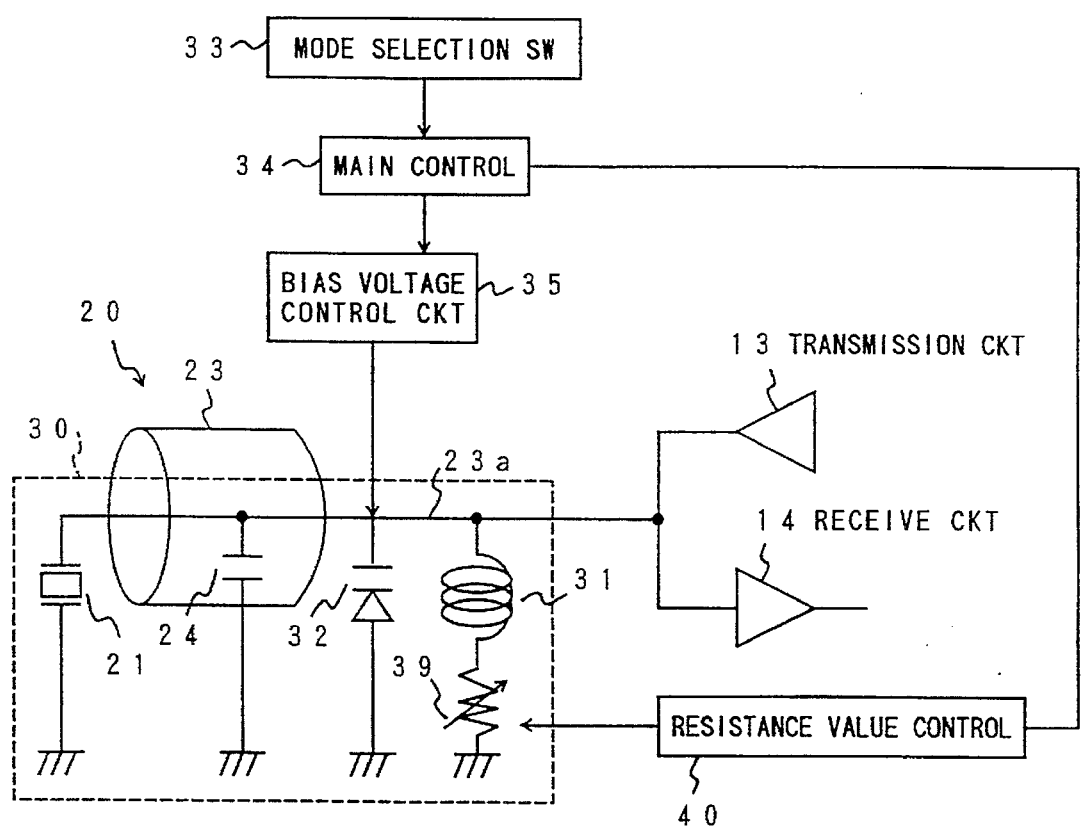
FIG. 12 is a circuit diagram of main parts of the eighth embodiment of the present invention.

FIG. 12 is a circuit diagram of main parts of the eighth embodiment of the present invention.

According to the eighth embodiment, there are provided both a variable capacitive diode 32 and the variable resistance 39 which is connected in series with the inductor 31. When the diagnostic mode is altered by the mode selection switch 33, the bias to be applied to the variable capacitive diode 32 is altered by the bias voltage control circuit 35 via the main control unit 34, so that the capacitance of the variable capacitive diode 32 is varied, whereby the resonance frequency $f_r$ of the resonance circuit is varied. At the same time, the resistance value of the variable resistance 39 is altered by the resistance value control unit 40 via the main control unit 34, whereby the Q value of the resonance circuit is also varied.

According to the eighth embodiment, when the B-mode is selected by the mode selection switch 33, the resonance frequency $f_r$ is set up to a frequency which is higher than the center frequency $f_c$ of the ultrasonic waves and the Q value is decreased. On the other hand, when the Doppler mode is selected by the mode selection switch 33, the resonance frequency $f_r$ is set up to a frequency which is equivalent to the center frequency $f_c$ of the ultrasonic waves and the Q value is increased. In this manner, in any of the B-mode and the Doppler mode, it is possible to obtain the suitable received signals.

Incidentally, while the eighth embodiment explained referring to FIG. 12 is also provided with the mode selection switch 33, it is acceptable that both the resonance frequency $f_r$ of the resonance circuit 30 and the Q value are varied in accordance with conditions other than the diagnostic mode.

Figure 13:
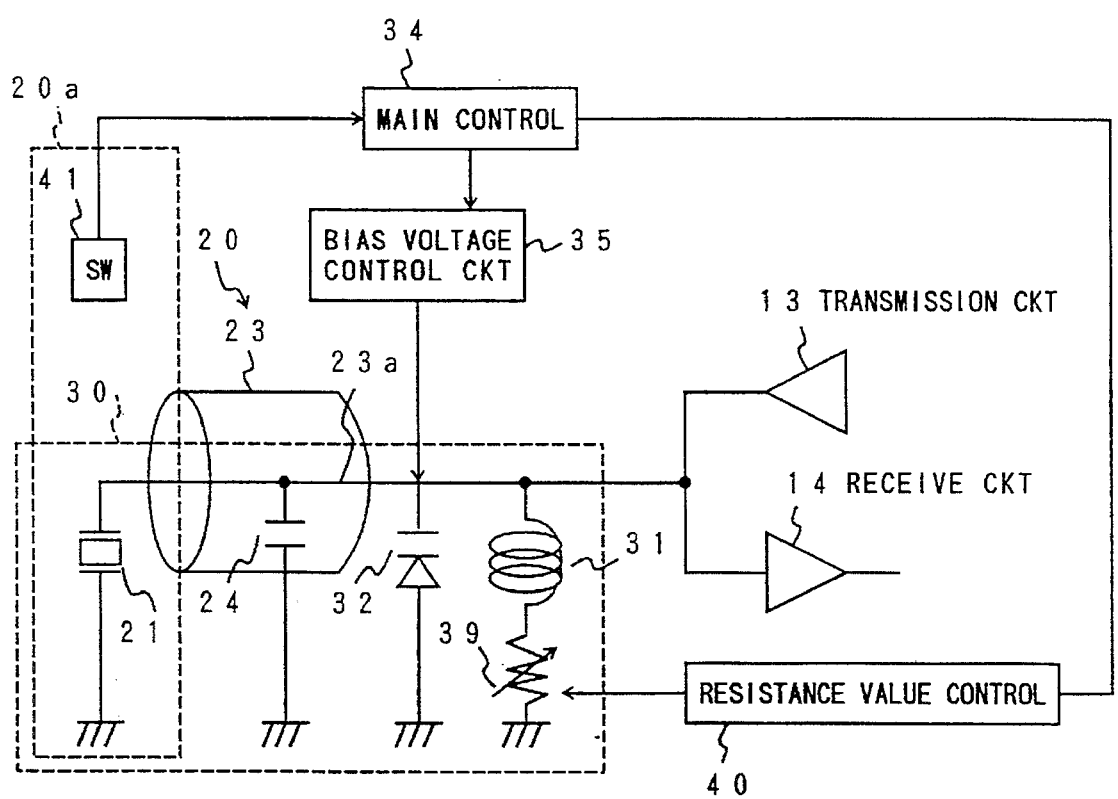
FIG. 13 is a circuit diagram of main parts of the ninth embodiment of the present invention.

FIG. 13 is a circuit diagram of main parts of the ninth embodiment of the present invention.

The difference between the ninth embodiment shown in FIG. 13 and the eighth embodiment shown in FIG. 12 resides in the point that there is provided a switch 41 on the tip portion 20a (FIG. 15) of the probe 20 only for the purpose of altering the characteristic of the resonance circuit 30, instead of the mode selection switch 33 adopted in the eighth embodiment.

According to the ninth embodiment, there is so arranged that the resonance frequency $f_r$ of the resonance circuit 30 and the Q value are continuously varied in accordance with time during which the switch 41 is operated. This arrangement makes it possible to adjust images displayed on the display screen 11 into the image which is most easy to see through operating the switch 41 while the operator 100 (FIG. 15) manually controls a position and an angle of the tip portion 20a of the probe 20 and in addition observes a tomographic image displayed on the display screen 11.

Figure 14:
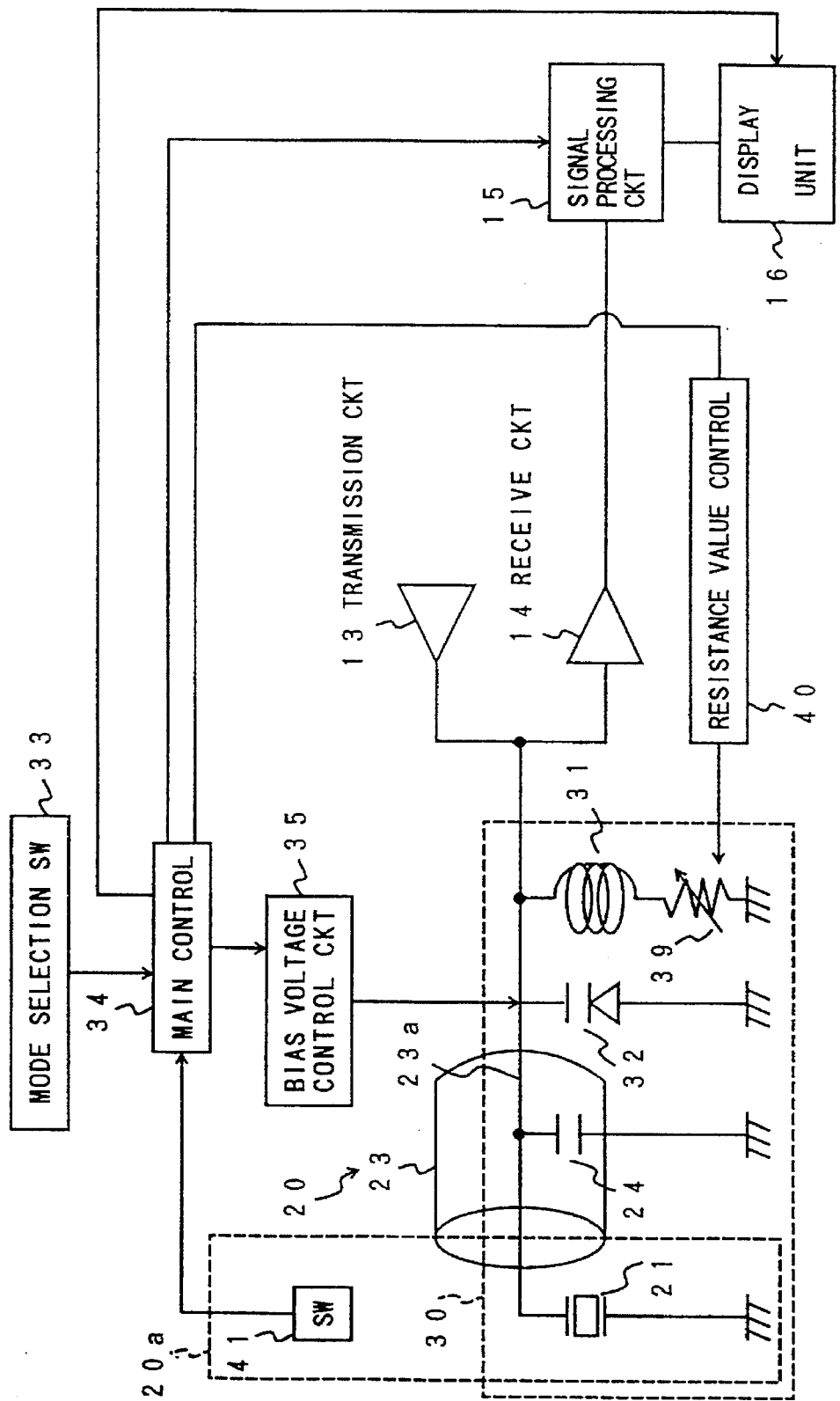
FIG. 14 is a circuit diagram of main parts of the tenth embodiment of the present invention.

FIG. 14 is a circuit diagram of main parts of the tenth embodiment of the present invention.

According to the tenth embodiment, in a similar fashion to that of eighth embodiment shown in FIG. 12, there is provided the mode selection switch 33, and in addition in a similar fashion to that of ninth embodiment shown in FIG. 13, there is provided the switch 41 on the tip portion 20a of the probe 20. The resonance frequency $f_r$ of the resonance circuit 30 and the Q value are varied in accordance with a mode switching through an operation of the mode selection switch 33, whereas the fine adjustment is implemented by the switch 41 in accordance with physique of the subject 200 (FIG. 15). Further, according to the tenth embodiment, information as to the resonance frequency $f_r$ of the resonance circuit 30 and the Q value, which have been now set up, is fed from the main control unit 34 to the display 16, so that the resonance frequency $f_r$ and the Q value, or the corresponding values, marks and the like are displayed on the display screen 11 (FIG. 15). This causes the operator 100 to recognize the photographic conditions with greater accuracy, thereby preventing mishandling.

As described above, according to the present invention, it is possible to provide an ultrasonic diagnostic apparatus capable of adapting to various uses with few probes and obtaining an extended definition of image.

While the present invention has been described with reference to the particular illustrative embodiments, it is not to be restricted by those embodiments but only by the appended claims. It is to be appreciated that those skilled in the art can change or modify the embodiments without departing from the scope and spirit of the present invention.

I claim:

1. An ultrasonic diagnostic apparatus comprising a probe having a signal transmission cable and a piezo-electric transducer for transmitting and receiving ultrasonic waves, said piezo-electric transducer being mounted on a tip of said signal transmission cable, and a main body for displaying images within a subject on the basis of received signals generated in such a manner that ultrasonic waves are transmitted from said piezo-electric transducer into the subject and the ultrasonic waves reflected within the subject are received by said piezo-electric transducer, a rear end of said probe being connected to said main body, said ultrasonic diagnostic apparatus further comprising:

a resonance circuit arranged in such a manner that at least the piezo-electric transducer and the signal transmission cable form a constituting element of the resonance circuit, said resonance circuit being located within said probe or extending through said probe and said main body, and permitting at least one of a resonance frequency and a Q value to be altered; and resonance characteristic altering means for altering at least one of the resonance frequency and the Q value of the resonance circuit in accordance with conditions.

2. An apparatus according to claim 1, wherein said resonance characteristic altering means alters at least one of the resonance frequency and the Q value of the resonance circuit in accordance with at least one selected from among a diagnostic mode, a frequency of ultrasonic waves, a kind of said probe, time elapsed for receiving of ultrasonic waves and a focal length.

3. An apparatus according to claim 1, wherein said resonance circuit is provided with a variable capacitance diode, and said resonance characteristic altering means alters the resonance frequency of the resonance circuit through controlling a voltage to be applied to said variable capacitance diode.

4. An ultrasonic diagnostic apparatus comprising a probe having a signal transmission cable and a piezo-electric transducer for transmitting and receiving ultrasonic waves, said piezo-electric transducer being mounted on a tip of said signal transmission cable, and a main body for displaying images within a subject on the basis of received signals generated in such a manner that ultrasonic waves are transmitted from said piezo-electric transducer into the subject and the ultrasonic waves reflected within the subject are received by said piezo-electric transducer, a rear end of said probe being connected to said main body, said ultrasonic diagnostic apparatus further comprising:

a resonance circuit arranged in such a manner that at least the piezo-electric transducer and the signal transmission cable form a constituting element of the resonance circuit, said resonance circuit being located within said probe or extending through said probe and said main body, and permitting at least one of a resonance frequency and a Q value to be altered;

a handler; and resonance characteristic altering means for altering at least one of the resonance frequency and the Q value of the resonance circuit in accordance with an operation of said handler.

5. An apparatus according to claim 4, wherein said handler is disposed on a tip portion of said probe, said piezo-electric transducer being mounted on said tip portion of said probe.

6. An apparatus according to claim 3, wherein said resonance circuit is provided with a variable capacitance diode, and said resonance characteristic altering means alters the resonance frequency of the resonance circuit through controlling a voltage to be applied to said variable capacitance diode.

7. An ultrasonic diagnostic apparatus comprising a probe having a signal transmission cable and a piezo-electric transducer for transmitting and receiving ultrasonic waves, said piezo-electric transducer being mounted on a tip of said signal transmission cable, and a main body for displaying images within a subject on the basis of received signals generated in such a manner that ultrasonic waves are transmitted from said piezo-electric transducer into the subject and the ultrasonic waves reflected within the subject are received by said piezo-electric transducer, a rear end of said probe being connected to said main body, said ultrasonic diagnostic apparatus further comprising:

a resonance circuit arranged in such a manner that at least the piezo-electric transducer and the signal transmission cable form a constituting element of the resonance circuit, said resonance circuit being located within said probe or extending through said probe and said main body, and permitting at least one of a resonance frequency and a Q value to be altered; and resonance characteristic altering means for altering at least one of the resonance frequency and the Q value of the resonance circuit in accordance with conditions, wherein said resonance circuit is provided with an inductor and a variable resistance, which are mutually connected in series and disposed between the signal transmission cable of said probe and a ground, and said resonance characteristic altering means alters the Q value of the resonance circuit through controlling a resistance value of said variable resistance.

8. An ultrasonic diagnostic apparatus comprising a probe having a signal transmission cable and a piezo-electric transducer for transmitting and receiving ultrasonic waves, said piezo-electric transducer being mounted on a tip of said signal transmission cable, and a main body for displaying images within a subject on the basis of received signals generated in such a manner that ultrasonic waves are transmitted from said piezo-electric transducer into the subject and the ultrasonic waves reflected within the subject are received by said piezo-electric transducer, a rear end of said probe being connected to said main body, said ultrasonic diagnostic apparatus further comprising:

a resonance circuit arranged in such a manner that at least the piezo-electric transducer and the signal transmission cable form a constituting element of the resonance circuit, said resonance circuit being located within said probe or extending through said probe and said main body, and permitting at least one of a resonance frequency and a Q value to be altered;

a handler; and resonance characteristic altering means for altering at least one of the resonance frequency and the Q value of the resonance circuit in accordance with an operation of said handler, wherein said resonance circuit is provided with an inductor and a variable resistance, which are mutually connected in series and disposed between the signal transmission cable of said probe and a ground, and said resonance characteristic altering means alters the Q value of the resonance circuit through controlling a resistance value of said variable resistance.

9. An ultrasonic diagnostic apparatus comprising a probe having a signal transmission cable and a piezo-electric transducer for transmitting and receiving ultrasonic waves, said piezo-electric transducer being mounted on a tip of said signal transmission cable, and a main body for displaying images within a subject on the basis of received signals generated in such a manner that ultrasonic waves are transmitted from said piezo-electric transducer into the subject and the ultrasonic waves reflected within the subject are received by said piezo-electric transducer, a rear end of said probe being connected to said main body, said ultrasonic diagnostic apparatus further comprising:

a resonance circuit arranged in such a manner that at least the piezo-electric transducer and the signal transmission cable form a constituting element of the resonance circuit, said resonance circuit being located within said probe or extending through said probe and said main body, and permitting at least one of a resonance frequency and a Q value to be altered; and resonance characteristic altering means for altering at least one of the resonance frequency and the Q value of the resonance circuit in accordance with conditions, wherein said resonance circuit is provided with a variable capacitance diode, and said resonance characteristic altering means alters the resonance frequency of the resonance circuit through controlling a voltage to be applied to said variable capacitance diode, and wherein said resonance circuit is provided with an inductor and a variable resistance, which are mutually connected in series and disposed between the signal transmission cable of said probe and a ground, and said resonance characteristic altering means alters the Q value of the resonance circuit through controlling a resistance value of said variable resistance.

10. An ultrasonic diagnostic apparatus comprising a probe having a signal transmission cable and a piezo-electric transducer for transmitting and receiving ultrasonic waves, said piezo-electric transducer being mounted on a tip of said signal transmission cable, and a main body for displaying images within a subject on the basis of received signals generated in such a manner that ultrasonic waves are transmitted from said piezo-electric transducer into the subject and the ultrasonic waves reflected within the subject are received by said piezo-electric transducer, a rear end of said probe being connected to said main body, said ultrasonic diagnostic apparatus further comprising:

a resonance circuit arranged in such a manner that at least the piezo-electric transducer and the signal transmission cable form a constituting element of the resonance circuit, said resonance circuit being located within said probe or extending through said probe and said main body, and permitting at least one of a resonance frequency and a Q value to be altered;

a handler; and resonance characteristic altering means for altering at least one of the resonance frequency and the Q value of the resonance circuit in accordance with an operation of said handler, wherein said resonance circuit is provided with a variable capacitance diode, and said resonance characteristic altering means alters the resonance frequency of the resonance circuit through controlling a voltage to be applied to said variable capacitance diode, and wherein said resonance circuit is provided with an inductor and a variable resistance, which are mutually connected in series and disposed between the signal transmission cable of said probe and a ground, and said resonance characteristic altering means alters the Q value of the resonance circuit through controlling a resistance value of said variable resistance.

11. An ultrasonic diagnostic apparatus comprising a probe having a signal transmission cable and a piezo-electric transducer for transmitting and receiving ultrasonic waves, said piezo-electric transducer being mounted on a tip of said signal transmission cable, and a main body for displaying images within a subject on the basis of received signals generated in such a manner that ultrasonic waves are transmitted from said piezo-electric transducer into the subject and the ultrasonic waves reflected within the subject are received by said piezo-electric transducer, a rear end of said probe being connected to said main body, said ultrasonic diagnostic apparatus further comprising:

a resonance circuit arranged in such a manner that at least the piezo-electric transducer and the signal transmission cable form a constituting element of the resonance circuit, said resonance circuit being located within said probe or extending through said probe and said main body, and permitting at least one of a resonance frequency and a Q value to be altered;

a handler; and resonance characteristic altering means for altering at least one of the resonance frequency and the Q value of the resonance circuit in accordance with conditions and an operation of said handler as well.

* * * * *